United States Patent
Ratcliff

[11] Patent Number: 6,114,398
[45] Date of Patent: Sep. 5, 2000

[54] PERSONAL LUBRICANT TO PREVENT AND STOP ITCHING

[76] Inventor: Perry A. Ratcliff, 7439 E. Lincoln Dr., Scottsdale, Ariz. 85253

[21] Appl. No.: 09/262,507

[22] Filed: Mar. 2, 1999

Related U.S. Application Data

[60] Provisional application No. 60/076,652, Mar. 3, 1998.

[51] Int. Cl.⁷ .................................................. A61K 31/075
[52] U.S. Cl. ............................................................. 514/714
[58] Field of Search .............................. 424/661, 52, 614, 424/613, 325, 422, 45; 514/557, 825, 931, 714, 39.8, 944; 166/291

[56] References Cited

U.S. PATENT DOCUMENTS

| | | | |
|---|---|---|---|
| 4,818,519 | 4/1989 | Ratcliff | 424/53 |
| 4,883,125 | 11/1989 | Wilson et al. | 166/291 |
| 4,956,184 | 9/1990 | Kross | 424/661 |
| 5,200,171 | 4/1993 | Ratcliff | 424/52 |
| 5,208,031 | 5/1993 | Kelly | 424/412 |
| 5,384,134 | 1/1995 | Kross et al. | 424/661 |
| 5,489,435 | 2/1996 | Ratcliff | 424/422 |
| 5,536,743 | 7/1996 | Borgman | 514/398 |
| 5,618,550 | 4/1997 | Ratcliff | 424/422 |
| 5,667,817 | 9/1997 | Kross | 424/661 |
| 5,741,525 | 4/1998 | Larsen | 424/616 |

OTHER PUBLICATIONS

"The Inhibitory Effect of Alcide®, An Antimicrobial Drug, On Protein Synthesis in *Escherichia coli*", by JoAnn Scatina and Mohamed S. Abdel–Rahman, *Journal of Applied Technology*, vol. 5, No. 6, 1985, p. 388–394.

*Primary Examiner*—Marianne M. Cintins
*Assistant Examiner*—Vickie Kim
*Attorney, Agent, or Firm*—Cahill, Sutton & Thomas P.L.C.

[57] ABSTRACT

A composition is formed of chlorine dioxide and a phosphate added to a mixture of glucono delta lactone, glycerin and hydroxyethyl cellulose to form a lubricant that will stop itching by killing Candida species and several other organisms known to colonize the vagina.

28 Claims, 1 Drawing Sheet

PERSONAL LUBRICANT TO PREVENT AND STOP ITCHING

CROSS-REFERENCE TO RELATED APPLICATIONS

The present application includes subject matter disclosed in and claims priority to a provisional application entitled "Personal Lubricant to Prevent an Stop Itching", assigned Ser. No. 60/076,652, filed Mar. 3, 1998.

INCORPORATION BY REFERENCE

The inventor hereby incorporates herein by reference to the following U.S. Pat. No. 4,818,519 entitled "Method and Composition for Prevention of Plaque Formation and Plaque Dependent Diseases", issued Apr. 4, 1989, U.S. Pat. No. 5,200,171 entitled "Oral Health Preparation and Method", issued Apr. 6, 1993 and U.S. Pat. No. 5,489,435 entitled "Composition for Treatment of Abnormal Conditions of the Epithelium of Bodily Orifices", issued Feb. 6, 1996. Each of these patents describe inventions by the present inventor.

BACKGROUND OF THE INVENTION

1. Field of the Invention

The present invention is directed to a method and composition for providing a personally applied lubricant to prevent and stop itching and, more particularly, to a method and composition for preventing and stopping vaginal itching.

2. Description of Related Art

Vaginal itching is a common complaint of women. The products available at the present time take a consequential time period to be effective. Thus, discomfort will continue for a period of time after topical application of an existing product.

Vaginal itching is primarily from *Candida albicans*. Other Candida species may complicate the problem. A petroleum jelly product is presently widely used by women to help alleviate itching and discomfort. However, petroleum jelly may adhere to the vaginal walls and mask the early symptoms of an infection.

Previously, by the use of acidified hypochlorous acid, it has been shown that the resultant solution will kill virus forms including *Herpes virus, Scrapie virus*, and human immuno virus. [1] While this solution may generate some chlorine dioxide, it is difficult to prepare and it is an inaccurate way to control dosage in situ. To provide a product which requires mixing of two solutions by the end user is commercially difficult and may result in an inaccurate and possibly unsafe preparation for human use. It is obvious to one skilled in the art that one has to have a product that is effective, does not require accurate chemical mixing in situ, and has shelf life stability for at least two years when sold commercially. Stabilized chlorine dioxide with sodium phosphate does not have these limitations. Consequently, a single stable solution capable of regulatory agency approval is far superior to the Alcide system described in the above referenced paper.

[1] "The inhibitory effect of Alcide®, an antimicrobial drug, on protein synthesis in *Escherichia coli*.", by Scatina J, Abdel-Rahman MS, Goldman E. *J Appl Toxicol* 1985 Dec; 5(6):388–94.

A widely used preparation sold over the counter under the trademark K-Y Jelly includes chlorhexidine and is considered an effective bactericide. It is considered by some a weak killer of polyanna virus but is generally considered not to be an effective viricide.

SUMMARY OF THE INVENTION

Chlorine dioxide in purified deionized water with a phosphate, such as trisodium phosphate, is added to a mixture of glucono delta lactone, glycerin and hydroxyethyl cellulose. Preferably, the mixture has a viscosity to render it easy to use with an applicator. The mixture is a lubricant that provides a safe way to replenish personal moisture that feels natural. It also helps enhance sexual pleasure at the same time it provides protection against vaginal itching through Candida kill. Inflammation will be reduced by eliminating hydrogen sulfide and methylmercaptan which are facilitating permeation agents for the penetration of lipopolysaccharide antigen into and through the epithelial wall of the vagina.

It is therefore a primary object of the present invention to provide a lubricant that will stop and/or prevent the development of itching from the vagina or other body parts.

Another object of the present invention is to provide a self-applied mixture that will terminate the clinical manifestations of itching.

Still another object of the present invention is to provide a mixture for twice weekly use that will prevent development of itching from the vagina or other body parts.

A further object of the present invention is to provide a mixture that replenishes personal moisture at the vagina while it kills Candida species.

A still further object of the present invention is to provide a mixture that feels natural and helps enhance sexual pleasure while killing Candida species.

These and other objects of the present invention will become apparent to those skilled in the art as the description thereof proceeds.

BRIEF DESCRIPTION OF THE DRAWINGS

The present invention will be described with specificity and clarity with reference to the following drawings, in which.

DESCRIPTION OF THE PREFERRED EMBODIMENT

Figure 1:
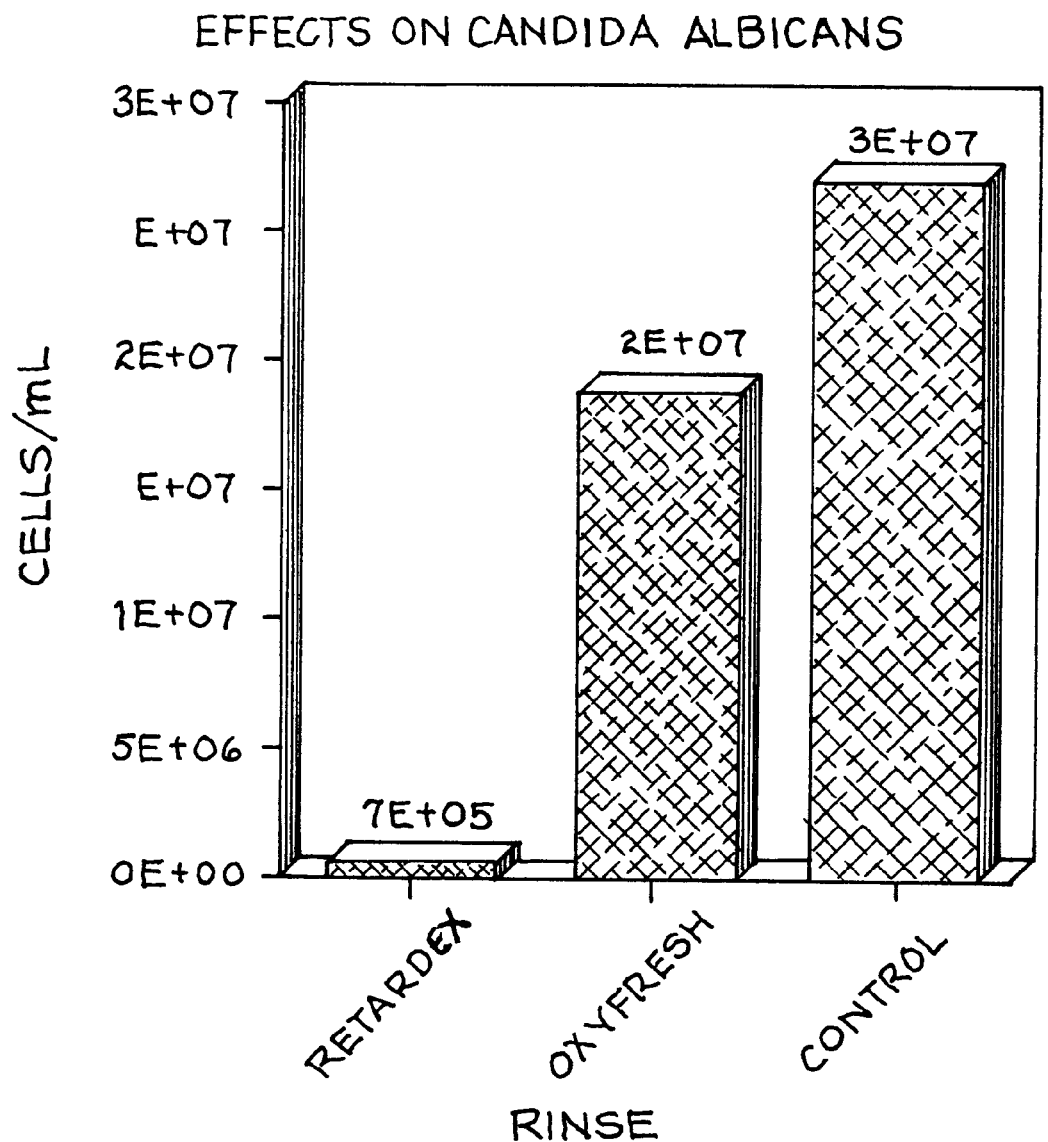
FIG. 1 illustrates the effectiveness on *Candida albicans* of two commercially available mouthrinses containing chlorine dioxide.

Vaginal itching is a common complaint of women. The products available today take a consequential period of time to be effective. The purpose of the present invention is to provide a more effective lubricant that will also treat and/or prevent the development of itching from the vagina or other body parts.

Vaginal itching is primarily from *Candida albicans*. Other Candida species may complicate the problem. Referring to FIG. 1, there is illustrated a graph depicting the effect on *Candida albicans* by two commercially available chlorine dioxide solutions. The research providing the data depicted in FIG. 1 was conducted to determine the efficiency of removal on *Candida albicans* by: 1) a mouthrinse sold under the trademark Retardex® by Rowpar Pharmaceuticals, Inc., and is described in further detail in U.S. Pat. No. 5,200,171 incorporated herein by reference; 2) Retardex® mouthrinse with domiphen bromide, and 3) a mouthrinse containing chlorine dioxide sold under the trademark Oxyfresh by Oxyfresh, USA.

METHOD

Culture Preparation:

*Candida albicans* ATCC 18804 was grown in Brain Heart Infusion broth (BBL) at 35° C. for 48 hours. After incubation, a serial dilution was performed onto Sabouraud Dextrose Agar (SDA) to obtain starting cell concentration.

Mouthwash Preparation:

Retardex® and Oxyfresh mouthrinses were used full strength. Retardex® mouthrinse plus domiphen bromide mouthrinse was diluted to a 50% solution with sterile distilled water.

Experiment:

The cells were washed three times with buffer and resuspended in 10 mls of buffer. For each test mouthwash and the control, 5 mls of serum were added to 5 mls of resuspended material and vortexed for 60 seconds. Consecutively, 1 ml of *C. albicans*-serum was added to 9 mls of each test mouthrinse. Buffer replaced the mouthrinse in the control. Vortexing continued as 1 ml aliquot was removed after a 30 second exposure to the test solutions and placed into 9 mls peptone +0.2% sodium thiosulfate diluent tube. A serial dilution was run using SDA. These plates were incubated at 35° C. for 48 hours. After incubation, cells were counted and recorded.

FIG. 1 illustrates the results of the effectiveness on *Candida albicans* of the Retardex® mouthrinse and the Oxyfresh mouthrinse after 30 seconds. The Retardex® mouthrinse showed a 97.5% kill compared to a 31.1% kill by the Oxyfresh mouthwash. In conclusion, the Retardex mouthwash was three times more effective than the Oxyfresh mouthwash.

Further clinical research acquired by the inventor has shown that a 0.1% chlorine dioxide solution can stop the growth of Candida species and it will terminate the clinical manifestations of itching. Continued use on a twice weekly basis will prevent the development of itching.

Unlike a widely used petroleum jelly (K-Y Jelly) which may adhere to vaginal walls and mask early symptoms of an infection, the composition described herein will produce a personal lubricant that provides a safe way to replenish personal moisture that feels natural and helps enhance sexual pleasure at the same time it provides protection against vaginal itching through Candida kill. It will also reduce inflammation by eliminating hydrogen sulfide and methylmercaptan which are facilitating permeation agents for the penetration of lipopolysaccharide antigen into and through the epithelial wall of the vagina and connecting tissue. A formula for this composition is a mixture of glucono delta lactone, glycerin and hydroxyethyl cellulose. To this is added chlorine dioxide in purified deionized water to give the mixture a viscosity for easy use with an applicator. An ideal formulation could be:

| | |
|---|---|
| Glycerin | 12.0% |
| Hydroxyethyl cellulose | 1.0% |
| Glucono delta lactone | 0.6% |
| Chlorine dioxide | 0.1% in deionized water |

An alternate formulation would be to substitute carboxymethyl cellulose for hydroxyethyl cellulose. Furthermore, the chlorine dioxide in deionized water could be replaced with an aqueous solution of chlorine dioxide and a phosphate, such as described in further detail in U.S. Pat. No. 5,200,171, incorporated herein by reference.

For commercial purposes, the stability of chlorine dioxide in the present composition is of significance. As set forth below, the stability of chlorine dioxide in three different carboxymethyl cellulose and trisodium phosphate based douche formulations were determined at 40 degrees C.

EXAMPLE 1

Materials:
1. $ClO_2$ (5% concentrated stock)
2. Carboxymethyl Cellulose—High, medium and low viscosity (Sigma).
3. Sodium phosphate, tribasic.
4. 1.0 N HCI.
5. 0.0250 N Sodium Thiosulfate ($Na_2S_2O_4$)

Methods:
1. 100 ml of each of the following solutions were prepared in deionized water:

| Solution | Percent CMC | Percent $ClO_2$* | Percent $Na_3PO_4$ |
|---|---|---|---|
| A | 4% low viscosity | 0.10% | 0.2% |
| B | 2% medium viscosity | 0.10% | 0.2% |
| C | 1% high viscosity | 0.10% | 0.2% |

2. Each solution was incubated at 40° C. for 30 days and the percent $ClO_2$ measured.
3. Each solution was incubated at 40° C. for an additional 30 days (60 days total) and the percent $ClO_2$ measured.

Results:

The results are set forth below in Table I.

TABLE I

| | Percent $ClO_2$ | | |
|---|---|---|---|
| Solution | Day 0 | Day 30 | Day 60 |
| A | 0.115% | 0.117% | 0.116% |
| B | 0.118% | 0.117% | 0.118% |
| C | 0.101% | 0.105% | 0.105% |

Conclusion:

The chlorine dioxide was stable in each of the three carboxymethyl cellulose and trisodium phosphate douche formulations. There were no significant decreases in the chlorine dioxide concentrations in any of the formulas when incubated at 40° C. for 30 or 60 days.

EXAMPLE 2

An experiment was conducted to determine bactericidal efficacy of a chlorine dioxide and phosphate composition added to K-Y jelly against several organisms known to colonize the vagina.

Materials:
1. Challenge Organisms
   a. *Neisseria gonorrhoeae* ATCC #430691
   b. *Peptostreptococcus lacrimalls* ATCC #51171
   c. *Gardnerella vaginalis* ATCC #14019
2. Butterfield's buffer
3. Sterile dilution tubes
4. Anaerobic Blood Agar Plates
5. Chocolate agar
6. Chlorine dioxide and phosphate composition was added to K-Y jelly manufactured by CITA International, Phoenix, Ariz.

Methods:
1. Bacterial suspensions were created from the reconstituted cultures of each organism into Butterfield's buffer.

2. 0.2 ml of stock suspension was added to 30 g of gel in 50 ml conical tubes.

3. The K-Y jelly was thoroughly mixed with a sterile stainless steel spatula.

4. 3.0 gram portions were removed at the desired time interval and neutralized with 1% sodium thiosulfate.

5. Neutralized solutions were then plated on the appropriate nutrient medium using the spread plate method. Plates were then incubated at 35° C. or 37° C. for 72 hours and enumerate.

Results:
Challenge Organism: *Neisseria gonorrhoeae*

| Test Description | Time 0 min | Time 1 min | Time 5 min | Time 30 min | Time 60 min |
|---|---|---|---|---|---|
| Control (cfu/ml) | 4,900,000 | 4,800,000 | 4,400,00 | 2,600,000 | 470,000 |
| K-Y Jelly (cfu/g) | 870,000 | 740,000 | 130,000 | <2,000 | <2,000 |
| Percent Kill | 82 | 85 | 97 | ≧99 | ≧99 |

Challenge Organism: *Gardnerella vaginalis*

| Test Description | Time 0 min | Time 1 min | Time 5 min | Time 30 min | Time 60 min |
|---|---|---|---|---|---|
| Control (cfu/ml) | 4,500,000 | 4,300,000 | 4,300,00 | 4,300,000 | 4,400,00 |
| K-Y Jelly (cfu/g) | 1,900,000 | <5,000 | <5,000 | <5,000 | <5,000 |
| Percent Kill | 58 | ≧99 | ≧99 | ≧99 | ≧99 |

Challenge Organism: *Peptostreptococcus lacrimalis*

| Test Description | Time 0 min | Time 1 min | Time 5 min | Time 30 min | Time 60 min |
|---|---|---|---|---|---|
| Control (cfu/ml) | 77,000,000 | 72,000,000 | 81,000,000 | 75,000,000 | 71,000,000 |
| K-Y Jelly (cfu/g) | 12,000,000 | <5,000 | <5,000 | <5,000 | <5,000 |
| Percent Kill | 85 | ≧99 | ≧99 | ≧99 | ≧99 |

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A composition for preventing and treating itching on a body part by reducing any of Candida species, *Neisseria gonorrhoeae* species, *Peptostreptococcus Lacrimalis* species, *Gardnerella Vaginalis* species present, said composition comprising a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

2. The composition as set forth in claim 1 wherein the phosphate compound is selected from the group consisting of disodium hydrogen phosphate, sodium dihydrogen phosphate, trisodium phosphate, sodium monofluorophosphate and pyrophosphate.

3. The composition as set forth in claim 1 wherein the concentration of the chlorine dioxide is in the range of between about 0.02% to about 3.0% and the concentration of the phosphate compound is in the range of about 0.02% to about 3.0%.

4. The composition as set forth in claim 1 wherein the composition comprises about 12% of glycerin, about 1.0% of the selected cellulose and about 0.06% of glucono delta lactone.

5. The composition as set forth in claim 4 wherein the phosphate compound is selected from the group consisting of disodium hydrogen phosphate, sodium dihydrogen phosphate, trisodium phosphate, sodium monofluorophosphate and pyrophosphate.

6. The composition as set forth in claim 4 wherein the concentration of the chlorine dioxide is in the range of between about 0.02% to about 3.0% and the concentration of the phosphate compound is in the range of about 0.02% to about 3.0%.

7. A method for preventing and treating itching on the vagina and adnexa tissue by reducing Candida species, said method comprising the step of applying a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

8. The method as set forth in claim 7 wherein the phosphate compound is selected from the group consisting of disodium hydrogen phosphate, sodium dihydrogen phosphate, trisodium phosphate, sodium monofluorophosphate and pyrophosphate.

9. The method as set forth in claim 7 wherein the concentration of the chlorine dioxide is in the range of between about 0.02% to about 3.0% and the concentration of the phosphate compound is in the range of about 0.02% to about 3.0%.

10. The method as set forth in claim 7 wherein the composition comprises about 12% of glycerin, about 1.0% of the selected cellulose and about 0.06% of glucono delta lactone.

11. A method for preventing and treating itching on a body part by reducing Candida species, said method comprising the step of applying a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

12. The method as set forth in claim 11 wherein the phosphate compound is selected from the group consisting of disodium hydrogen phosphate, sodium dihydrogen phosphate, trisodium phosphate, sodium monofluorophosphate and pyrophosphate.

13. The method as set forth in claim 11 wherein the concentration of the chlorine dioxide is in the range of between about 0.02% to about 3.0% and the concentration of the phosphate compound is in the range of about 0.02% to about 3.0%.

14. The method as set forth in claim 11 wherein the composition comprises about 12% of glycerin, about 1.0% of the selected cellulose and about 0.06% of glucono delta lactone.

15. The method as set forth in claim 14 wherein the phosphate compound is selected from the group consisting of disodium hydrogen phosphate, sodium dihydrogen phosphate, trisodium phosphate, sodium monofluorophosphate and pyrophosphate.

16. The method as set forth in claim 14 wherein the concentration of the chlorine dioxide is in the range of between about 0.02% to about 3.0% and the concentration of the phosphate compound is in the range of about 0.02% to about 3.0%.

17. A method for preventing and treating itching on the vagina and adnexa tissue by reducing *Neisseria Gonorrhoeae* species, said method comprising the step of applying a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

18. The method as set forth in claim 17 wherein the phosphate compound is selected from the group consisting of disodium hydrogen phosphate, sodium dihydrogen phosphate, trisodium phosphate, sodium monofluorophosphate and pyrophosphate.

19. The method as set forth in claim 17 wherein the concentration of the chlorine dioxide is in the range of between about 0.02% to about 3.0% and the concentration of the phosphate compound is in the range of about 0.02% to about 3.0%.

20. The method as set forth in claim 17 wherein the composition comprises about 12% of glycerin, about 1.0% of the selected cellulose and about 0.06% of glucono delta lactone.

21. A method for preventing and treating itching on the vagina and adnexa tissue by reducing *Peptostreptococcus Lacrimalls* species, said method comprising the step of applying a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

22. The method as set forth in claim 21 wherein the phosphate compound is selected from the group consisting of disodium hydrogen phosphate, sodium dihydrogen phosphate, trisodium phosphate, sodium monofluorophosphate and pyrophosphate.

23. The method as set forth in claim 21 wherein the concentration of the chlorine dioxide is in the range of between about 0.02% to about 3.0% and the concentration of the phosphate compound is in the range of about 0.02% to about 3.0%.

24. The method as set forth in claim 21 wherein the composition comprises about 12% of glycerin, about 1.0% of the selected cellulose and about 0.06% of glucono delta lactone.

25. A method for preventing and treating itching on the vagina and adnexa tissue by reducing *Gardnerella Vaginalis* species, said method comprising the step of applying a lubricant containing glycerin, a cellulose selected from the group of hydroxyethyl cellulose and carboxymethyl cellulose, glucono delta lactone, chlorine dioxide and a phosphate compound to retard escape of chlorine dioxide from the composition at a pH in the range of 6.0 to 7.4.

26. The method as set forth in claim 25 wherein the phosphate compound is selected from the group consisting of disodium hydrogen phosphate, sodium dihydrogen phosphate, trisodium phosphate, sodium monofluorophosphate and pyrophosphate.

27. The method as set forth in claim 25 wherein the concentration of the chlorine dioxide is in the range of between about 0.02% to about 3.0% and the concentration of the phosphate compound is in the range of about 0.02% to about 3.0%.

28. The method as set forth in claim 25 wherein the composition comprises about 12% of glycerin, about 1.0% of the selected cellulose and about 0.06% of glucono delta lactone.

* * * * *